United States Patent
Benozzi

(10) Patent No.: US 8,524,758 B2
(45) Date of Patent: Sep. 3, 2013

(54) OPHTHALMIC COMPOSITIONS OF PARASYMPATHETIC STIMULANTS AND ANTI-INFLAMMATORIES FOR USE IN THE TREATMENT OF PRESBYOPIA

(76) Inventor: Jorge Luis Benozzi, Buenos Aires (AR)

( * ) Notice: Subject to any disclaimer, the term of this patent is extended or adjusted under 35 U.S.C. 154(b) by 0 days.

(21) Appl. No.: 12/519,910

(22) PCT Filed: Dec. 6, 2007

(86) PCT No.: PCT/IB2007/003780
§ 371 (c)(1),
(2), (4) Date: Aug. 10, 2009

(87) PCT Pub. No.: WO2008/075149
PCT Pub. Date: Jun. 26, 2008

(65) Prior Publication Data
US 2010/0016395 A1    Jan. 21, 2010

(30) Foreign Application Priority Data
Dec. 18, 2006   (EP) .................................. 06026169

(51) Int. Cl.
*A61K 31/195* (2006.01)
*A61K 31/415* (2006.01)

(52) U.S. Cl.
USPC .......................... 514/397; 514/567; 514/912

(58) Field of Classification Search
USPC ......................... 514/397, 567, 912
See application file for complete search history.

(56) References Cited

U.S. PATENT DOCUMENTS

| | | | |
|---|---|---|---|
| 5,422,116 A * | 6/1995 | Yen et al. ..................... | 424/427 |
| 5,488,050 A | 1/1996 | Neufeld | |
| 6,258,082 B1 | 7/2001 | Lin | |
| 6,263,879 B1 | 7/2001 | Lin | |
| 6,273,092 B1 | 8/2001 | Nolan | |
| 6,291,466 B1 * | 9/2001 | Gwon et al. ................... | 514/256 |
| 2005/0119262 A1 * | 6/2005 | Wax ........................... | 514/235.5 |
| 2005/0205101 A1 * | 9/2005 | Lin ............................. | 128/898 |

FOREIGN PATENT DOCUMENTS

WO    00/06135    2/2000

OTHER PUBLICATIONS

Benozzi et al., "Presbyopia: a New Potential Pharmacological Treatment," Medical Hypothesis, Discovery & Innovation Ophthalmology Journal (2012) 1(1):3-5.
Croft et al., "Accommodation and Presbyopia," International Ophthalmology Clinics (2001) 41(2): 33-46.
Glasser, A., "Accommodation: Mechanism and Measurement," Ophthalmology Clinics of North America (2006) 19:1-12.
Garner et al., "Changes in ocular dimensions and refraction with accommodation," Ophthal Physiol Opt. (1997) 17(1): 12-17.
Koeppl et al., "Comparision of pilocarpine-induced and stimulus-driven accommodation in phakic eyes," Experimental Eye Research (2005) 80:795-800.
Pardue et al., "Age-Related Changes in Human Ciliary Muscle," Optomerty and Vision Science (2000) 77(4): 204-210.
Croft et al., "Accommodation and Ciliary Muscle Muscarinic Receptors After Echothiophate," Investigative Ophthalmology & Visual Science (1991) 32(13): 3288-3297.
Ostrin et al., "Comparisons between Pharmacologically and Edinger-Westphal-Stimulated Accommodation in Rhesus Monkeys," Investigative Ophthalmology & Visual Science (2005) 46(2): 609-617.
Mathews, S., "Scleral Expansion Surgery does Not Restore Accommodation in Human Presbyopia," Ophthalmology (1999) 106(5): 873-877.
Koopmans et al., "Polymer Refilling of Presbyopic Human Lenses In Vitro Restores the Ability to Undergo Accommodative Changes," Investigative Ophthalmology & Visual Science (2003) 44(1): 250-257.
Schalnus, R., "Topical Nonsteroidal Anti-Inflammatory Therapy in Ophthalmology," Ophthalmologica (2003) 217:89-98.
Zimmerman et al., "Miotics: side effects and ways to avoid them," Ophthalmology (1982) 89(1): 76-80 (Abstract only).
Jabs, D., "Treatment of ocular inflammation," Ocular Immunology and Inflammation (2004) 12(3): 163-168.
Ostrin, L. A. et al., "Pilocarpine Stimulated Accommodation in Humans", Database accession No. PREV200300154537, Annual Meeting Abstract Search and Program Planner, vol. 2002, Abstract No. 2317, Annual Meeting of the association for research in vision and Ophthalmology, Fort Lauderdale, Florida, USA, May 5-10, 2002., pp. 1-2.

* cited by examiner

*Primary Examiner* — Zohreh Fay
(74) *Attorney, Agent, or Firm* — Volpe and Koenig, P.C.

(57) ABSTRACT

Ophthalmic compositions for the treatment of presbyopia, including combinations of parasympathomimetics and non-steroidal anti-inflammatories.

12 Claims, No Drawings

OPHTHALMIC COMPOSITIONS OF PARASYMPATHETIC STIMULANTS AND ANTI-INFLAMMATORIES FOR USE IN THE TREATMENT OF PRESBYOPIA

The present invention relates to ophthalmic compositions comprising parasympathetic stimulants and non-steroidal anti-inflammatories for use in the treatment of presbyopia.

PRIOR ART

Presbiopia, a defect in accommodation, has traditionally been treated with the use of corrective lens.

In recent years, surgery methods such as scleral expansion band, anterior ciliary sclerotomy, multifocal intraocular lenses or laser ablation of sclera retrolimbare (U.S. Pat. Nos. 6,263,879 and 6,258,082) have been suggested to correct presbyopia. All of such techniques are, however, controversial, as they do not solve the mechanical problem of accommodation (Mathews S., *Scleral Expansion Surgery does not Restore Accommodation in Human Presbyopia. Ophthalmology* 1999; 106: 873-877).

Publications concerning the treatment of presbyopia do not take into account such mechanism and aim at a surgical correction of near vision.

Lin-Kadambi suggest sympathetic and parasympathetic stimulation with adrenergic and cholinergic drugs to pharmacologically assist stabilization of the surgical results. Pharmacological treatment to treat accommodation in man has been reported in previous articles.

According to Rosenfield, treatment with an alpha-adrenergic antagonist induced an increase in accommodative amplitude of 1.5 D. Said action, however, only lasts two hours (Rosenfield M. The influence of Alpha-adrenergic-agents on tonic accommodation. Current Eye Research, vol. 9, 3, 1990, pp. 267-272).

According to Nyberg, van Alphen et al., therapy with alpha-adrenergic-agents was not satisfactory in presbyopic patients.

Nolan (U.S. Pat. No. 6,273,092) reports that topical application of acetylcholine and physostygmine to presbyopic patient gives poor results and does not solve blurred distant vision.

DISCLOSURE OF THE INVENTION

The present invention relates to the pharmacological treatment of presbyopia, without surgical intervention.

It has in fact been found that alterations of visual accommodation can be treated by stimulating the sympathetic innervation which induces accommodation for near vision by use of parasympathomimetics and that said results can be maintained in time by treatment with non-steroidal anti-inflammatories (NSAIDs).

According to the invention, non-steroidal anti-inflammatories can be selected from the group consisting of diclofenac, ketorolac, bromfenac, flurbiprofen, suprofen, pranoprofen, oxyphenbutazone, bendazac, indomethacin.

Therefore, the present invention relates to ophtalmic compositions comprising combinations of parasympathomimetics and non-steroidal anti-inflammatories for the treatment of presbyopia.

The parasympathomimetics present in the combinations of the invention act on the contraction/relaxation strength of the ciliary muscle thus keeping accommodation levels stable, while NSAIDs preserve such action in time, preventing those physiological degenerations typically occurring in time with presbyopic subjects. The combinations of the invention prevent any histological and physical alterations (fibrosis and rigidity) in the ciliary muscle-zonula complex.

The present invention provides successful, stable results in emmetropic and hypermetropic patients for at least five years; on the other hand, the invention is unsuccessful when shape modification of the lens is prevented by its rigidity.

More particularly, the present invention relates to ophthalmic compositions of pilocarpine and a NSAID for use in the treatment of presbyopia.

According to a preferred aspect of the invention, pilocarpine is in form of its hydrochloride and the NSAID is diclofenac sodium.

The compositions of the invention will contain the parasympathomimetic agent in amounts ranging from 0.5% to 4% and the NSAID in amounts ranging from 0.01 mg. to 0.1 mg.

According to a preferred aspect of the invention, the compositions will contain pilocarpine hydrochloride in concentrations ranging from 1% to 2% and diclofenac sodium in amounts ranging from 0.1% to 0.5%.

The ophthalmic compositions will be suitably formulated for the topical administration, according to well known procedure and techniques, such as those described in "Remington's Pharmaceutical Handbook", 18th edition (June 1995), Mack Publishing Co., N.Y., USA, using conventional additives well known in the pharmaceutical technique. Example of said additives are isotonic agents, such as propylene glycol, sodium chloride, potassium chloride, glycerine, sorbitol, mannitol, and the like; buffers, such as boric, phosphoric, acetic, carbonic, citric acids, and the like; stabilizers, such as ethylenediaminetetraacetic acids, sodium hydrogen sulphite, and the like; pH agents, such as citric, phosphoric, hydrochloric, acetic acids, sodium or potassium hydroxide, sodium carbonate or bicarbonate, and the like; solubilizers, such as polysorbate, polyethylene glycol, propylene glycol, macrogol 4000, and the like; thickening and dispersing agents, such as cellulose derivatives, sodium alginate, polyvinyl alcohol, carboxyvinylpolymer, polyvinyl pyrrolidone, and the like.

The results of the pharmacological experimentation with the compositions of the invention are reported the following.

Materials and Methods

100 Presbiopic patients of both sexes, of age 40 to 65, were treated with the compositions of the invention. Exclusion criteria concerned patients with myopia or astigmatism higher than 1 dioptre, and hypermetropia greater than 3 dioptres as well as those with corneal, lens and vitreous opacitis, and chronic general pathologies.

4 Different groups of presbyopic population were differentiated:

Group 1: Pure presbyopics
Group 2: Presbyopics with hypermetropia
Group 3: Presbyopics with phorias
Group 4: Presbyopics with glaucoma Patients of all groups were treated with eye drops of different concentrations and combinations of medicaments acting on the ocular sympathetic innervation.

Pure presbyopic patients (Group 1) were topically treated with 1% pilocarpine hydrochloride+0.5% diclofenac sodium, at 6 hr intervals during the daily hours; treatment was suspended at night.

Presbyopics with hypermetropia (Group 2) were topically treated with 2% pilocarpine hydrochloride+0.5% diclofenac sodium, at 6 hr intervals during the daily hours.

Presbyopic patients with phorias (Group 3) were topically treated with 1% pilocarpine hydrochloride at 6 hr intervals during the daily hours, together with an orthoptic treatment directed to stimulate fusion and accommodation-convergence. This orthoptic treatment was performed by training the patient in the use of an exercising software, which then the patient used without the need of professional help. 3-Minute sessions were carried out daily for a period of 15 days and were repeated yearly.

Presbyopics patients with glaucoma (Group 4), were topically treated with 2% pilocarpine hydrochloride+0.5% diclofenac sodium at 6 hr intervals during the 24 hours i.e. including nighttime. Regular hypotensive medication used by the patients was maintained.

All patients were monitored after one week treatment and monthly during the first three months to evaluate dosage and side-effects.

Controls included:
Near and distant visual sharpness
Myosis
Conjunctiva
Ocular tension
Astenopia
Tolerance
When visual sharpness was not desired, dosages were changed and accommodation was checked.
When myosis was not tolerated, argon laser iridoplasty was carried out by shooting in 360° spots in the iris constrictor muscle. The laser intensity and the size of the spot, were adapted to the intensity of iris pigmentation.
Topical treatment was modified in case of conjunctiva inflammation.
When ocular tension was not ideal, hypotensive medication was modified prior to presbyopia treatment.
Orthoptic treatment was corrected in case of patient astenopia.
Treatment was suspended in case of intolerance to medication.

Results and Conclusions

100 Patients were treated: 2 patients showed intolerance to pilocarpine hydrochloride (diarrhoea and dyspepsia), 2 patients (presbyopics with hypermetropia) did not obtain the desired improvement in visual sharpness.

10 patients have been under treatment for 6 years
20 patients have been under treatment for 5 years
30 patients have been under treatment for 4 years
40 patients have been under treatment for 3 years
80 patients have been under treatment for 2 years
96 patients have been under treatment for 1 year.

Results

Group 1: 100% of patients experienced correction of presbyopia.

Group 2: 48% of patients abandoned the use of eyeglasses, 44% only use eyeglasses for near vision with 2 to 3 dioptres less than those required before treatment, according to their original hypermetropy, and 8% of patients abandoned treatment.

Group 3: 89.47% of patients abandoned eyeglasses and have good near vision, 10.53% did not experience improvements in their near vision.

Group 4: 100% of patients had good near vision without glasses and maintained their ocular hypertension under control.

Patients who discontinued the treatment experienced regression of visual sharpness to that before treatment. No worsening of presbyopia was observed, conversely in some patients accommodation was better than before starting treatment.

The invention claimed is:

1. A medicament for the treatment of presbyopia comprising a parasympathomimetic agent and a non-steroidal anti-inflammatory agent, wherein the parasympathomimetic agent is pilocarpine or a salt thereof present at a concentration ranging from 0.5% to 4% and the non-steroidal anti-inflammatory agent is diclofenac or a salt thereof in an amount ranging from 0.01 mg to 0.1 mg.

2. The medicament of claim 1, wherein the non-steroidal anti-inflammatory agent is present at a concentration ranging from 0.1% to 0.5% or at a concentration of 0.5%.

3. The medicament of claim 1, wherein the parasympathomimetic agent is present at a concentration ranging from 1% to 2%.

4. The medicament of claim 3, wherein the non-steroidal anti-inflammatory agent is at a concentration of 0.5%.

5. The medicament of any one of claims 1, 2, 3, or 4, wherein the parasympathomimetic agent is pilocarpine hydrochloride.

6. The medicament of claim 5, wherein the non-steroidal anti-inflammatory agent is diclofenac sodium.

7. The medicament of any one of claims 1, 2, 3, 4, or 6 wherein the medicament further comprises at least one pharmaceutical additive selected from the groups consisting of isotonic agent, buffer, stabilizer, pH agent, solubilizer, thickening agent and dispersing agent.

8. The medicament of claim 7, wherein the medicament is an ophthalmic composition.

9. An ophthalmic composition for the treatment of presbyopia comprising pilocarpine or a salt thereof, diclofenac or a salt thereof, and at least one pharmaceutical additive selected from the group consisting of isotonic agent, buffer, stabilizer, pH agent, solubilizer, thickening agent and dispersing agent, wherein the pilocarpine or a salt thereof is present at a concentration ranging from 0.5% to 4% and diclofenac or a salt thereof is present at a concentration ranging from 0.1% to 0.5%.

10. The ophthalmic composition of claim 9, wherein pilocarpine is present at a concentration ranging from 1% to 2%.

11. The ophthalmic composition of claim 9, wherein the pilocarpine salt is pilocarpine hydrochloride.

12. The ophthalmic composition of claim 11, wherein the diclofenac salt is diclofenac sodium.

* * * * *